United States Patent [19]

Scheinberg

[11] 3,943,923
[45] Mar. 16, 1976

[54] SPLINT AND METHOD OF APPLYING SAME
[75] Inventor: Samuel Scheinberg, Lincoln City, Oreg.
[73] Assignee: Lawrence A. Atler, Denver, Colo.; a part interest
[22] Filed: Oct. 10, 1974
[21] Appl. No.: 513,857

Related U.S. Application Data
[63] Continuation-in-part of Ser. No. 261,059, June 8, 1972, abandoned.

[52] U.S. Cl. ............................................. 128/89 R
[51] Int. Cl.² .......................................... A61F 5/04
[58] Field of Search .......... 128/89 R, 87, 77, 82, 90

[56] References Cited
UNITED STATES PATENTS

| | | | |
|---|---|---|---|
| 1,144,103 | 6/1915 | Brant | 128/87 A |
| 1,617,942 | 2/1927 | Foulke | 128/87 A |
| 2,506,464 | 5/1950 | Millheisler | 128/89 R |
| 3,189,025 | 6/1965 | Yaklin | 128/77 X |

OTHER PUBLICATIONS
Orthopaedic Appliances Atlas, pp. 306, 307, Fig. 434, 1952.
Richards Fracture & Orthopedic Supplies Catalogue, p. 24 1966.

Primary Examiner—John D. Yasko
Attorney, Agent, or Firm—Bertha L. MacGregor

[57] ABSTRACT

Disclosed herein is a splint comprising an elongated rectangular flat strip of malleable metal having a width sufficient to embrace the major width of an extremity such as an arm, a leg or a finger, and of thickness insufficient to provide requisite rigidity for a splint. The strip is initially rollable or foldable into a compact package for storage or shipment. When unrolled or unfolded into flat form, for application to an injured extremity, the strip is bent manually transversely between its ends to provide two legs connected by said transversely curved area, and the legs are manually then bent or folded longitudinally approximately midway between the longitudinal edges of the legs into U-form, said longitudinal bends or folds extending from the leg ends to the opposite sides of said transversely curved connecting area into which they merge. The said manually produced longitudinal bends result in non-uniform U-shaped transverse cross sections in the legs and impart splint-serving rigidity to the legs. The non-uniform character of the longitudinal U-shaped bends in the legs produces interrupted contact surfaces which permit passage of air between the splint and skin of the extremity to which it has been applied.

5 Claims, 6 Drawing Figures

U.S. Patent  March 16, 1976  3,943,923
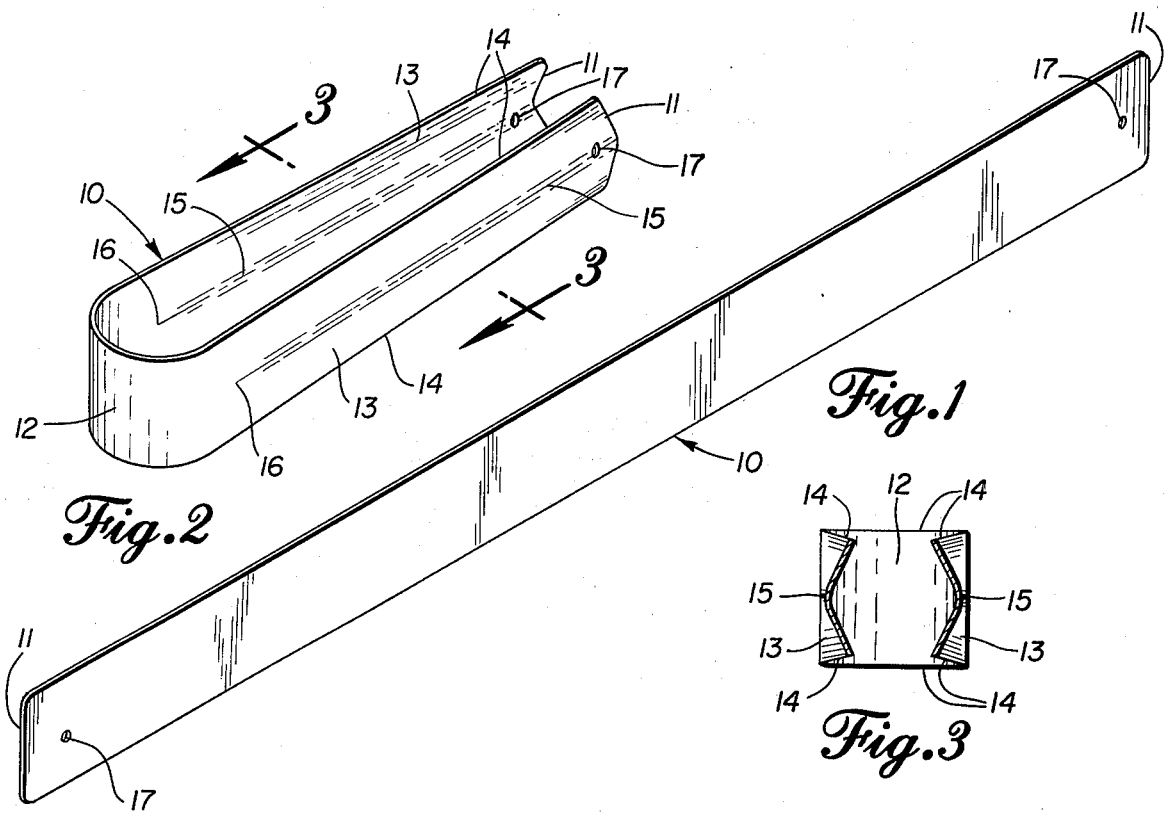
Fig.1
Fig.2
Fig.3
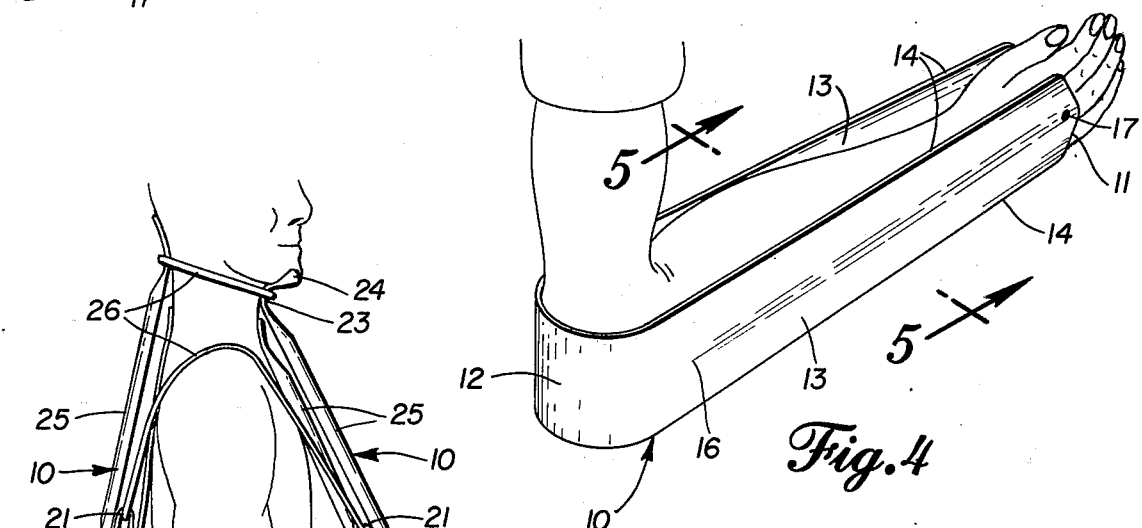
Fig.4
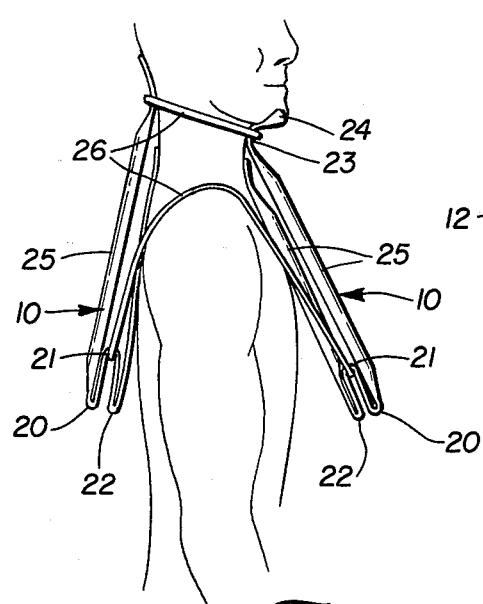
Fig.6
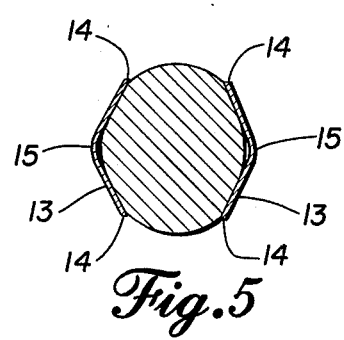
Fig.5

SPLINT AND METHOD OF APPLYING SAME

This application is a continuation-in-part of Ser. No. 261,059, filed June 8, 1972 now abandoned.

BACKGROUND AND SUMMARY OF THE INVENTION

This invention relates to a splint made of an elongated rectangular flat strip of malleable metal, such as aluminum, which is wide enough to embrace an arm, a leg or a finger, but insufficient in thickness to provide requisite rigidity to serve as a splint. The strip is initially rollable or foldable into a compact package for storage or shipment. When unrolled or unfolded to flat form, preparatory to application on an injured extremity, the strip is first manually folded or bent transversely between its ends to provide two legs connected by said transversely curved area, and the legs are then manually bent or folded longitudinally approximately midway between the longitudinal edges of the legs into U-form, said longitudinal bends or folds extending from the leg ends to the opposite sides of said transversely bent connecting area into which they merge. The manually shaped longitudinal folds or bends produce non-uniform U-shaped transverse cross sections in the legs and impart splint-serving rigidity to the legs. The non-uniform character of the manually formed longitudinal U-shaped bends in the legs produces interrupted contact surfaces which permit passage of air between the splint and skin of the extremity to which the splint has been applied. For application to arms, legs and fingers, the convex surfaces of the two legs face each other at opposite sides of the extremity; for other applications, such as neck injuries, the legs may be given longitudinal bends or folds which make the convex surfaces of the legs face away from each other or toward each other, as required by the particular injury.

Description of the Prior Art

Prior art splints comprising flat metal strips have been known, but the legs of such splints have not had manually produced, non-uniform skin-contacting surfaces which are the result of the manula bending or folding longitudinally between the longitudinal edges of the legs, said folds or bends extending from the free ends of the legs to the opposite sides of the previously manually produced transverse bend which connects the tow legs. An example of prior art structures of the type noted is disclosed in U.S. Pat. No. 2,506,464, in which two pivotally connected strips provide four legs for splinting a finger, and the legs are slightly curved transversely to provide stiffness to the legs and to provide a formed curvature in the stall for close fitting around the injured member. The formed curvature in the legs of this prior art device is of a uniform, machine formed character, not manually shaped, as distinguished from the manually formed longitudinal bends or folds which produce non-uniform transverse cross sections throughout the legs of this invention between the free ends of the legs and the opposite sides of the transverse bend or fold previously manually placed in the strip.

Other commonly used splints are made of straight wooden pieces, cardboard, and other materials, which cannot be washed, are unsanitary and cumbersome. Their unyielding character produces uninterrupted contact with the skin of the injured member, preventing air circulation essential to comfort.

The novel coating of the metallic strip employed in this invention, described hereinafter, renders the splint washable and re-usable, and permits X-ray of the injured member without removal of the splint.

In the drawings:

FIG. 1 is an elevational side view of an elongated rectangular flat strip of malleable metal from which the splint embodying my invention is made.

FIG. 2 is an isometric view of a splint embodying my invention made by bending the strip shown in FIG. 1.

FIG. 3 is a transverse sectional view in the plane of the line 3—3 of FIG. 2.

FIG. 4 is an isometric view of the splint of FIG. 2 applied to a patient's arm.

FIG. 5 is a transverse sectional view in the plane of the line 5—5 of FIG. 4.

FIG. 6 is an elevational side view of two splints embodying the invention, one applied to the chest and neck of a patient and the other to the back and neck.

DESCRIPTION OF THE PREFERRED EMBODIMENT

In the embodiment of the invention shown in the drawings, an elongated flat rectangular strip 10 of malleable metal, such as annealed aluminum, is coated with a material which is radiolucent and which protects the metal from corrosion, prevents sticking to the skin, and which is non-allergenic and washable. A coating of polyvinyl chloride applied to the metal strip in liquid form and cured to solid state has been found suitable for its intended purpose and permits the extremity to be x-rayed without removing the splint.

The width of the strip 10 is sufficient to substantially embrace the major width of the injured extremity and of a thickness insufficient to provide requisite rigidity for a splint, but the subsequent manual bending and folding of the strip 10 transforms it into an efficient splint-serving structure suitable for application to fingers, arms and legs, as well as for supporting necks and chins, with adequate resistance against flexure.

In its initial flat form, the relatively thin, coated metal strip 10 is rollable and bendable into a compact package for convenient storage and shipment.

For application to an injured extremity, the strip 10 is first bent manually transversely between its ends 11, 11, as indicated at 12, thereby providing two legs 13, 13, each having longitudinal edges 14, 14. The legs 13 are connected by the transversely curved portion 12 which is manually bent and molded to extend around an elbow or under a foot or across the tip of an injured finger.

Next each of the legs 13 is manually bent longitudinally approximately midway between its longitudinal edges 14 as indicated by the longitudinal fold 15 which extends from the leg end 11 to a point 16 near the transverse bend 12, where the fold 15 merges into said curved area 12. The longitudinal fold 15 produces U-shaped transverse cross sections in the legs 13 which are non-uniform in that the bight of the U-shape varies but is of sufficient depth to impart splint-serving rigidity to the legs 13 throughout their length, whether applied to a small short part such as a finger or a larger long part such as a leg. The longitudinal fold 15 is manually formed into U-shaped cross sections in each of the two legs, having the convex surfaces facing each other for application to extremities such as legs, arms and fingers. The transverse width of the longitudinal fold 15 varies, and since it is manually formed the sections are non-uniform. The fact that the transverse cross sections of the legs, between the transversely curved area 12 and the end edges 11, are non-uniform is advantageous because the convex surfaces thus have interrupted contact with the skin of the patient which permits passage of air adjacent the skin without detracting from the efficiency of the structure to serve as a splint.

The manually bent or molded longitudinal fold 15 gradually decreases in transverse width as it tapers toward the area 16 of the transverse fold 12. After application to the injured extremity, further manual molding by pressing on the leg surfaces at opposite sides of the fold 15 may be done, but the effective stiffening of the legs to give them required rigidity is achieved by the bending of the legs longitudinally at 15 into U-shaped transverse cross sections between the ends 11 and the transversely curved area 12.

In FIG. 6 is shown apparatus for splinting a neck. This includes two splints made of two strips 10 heretofore described. One strip 10 is bent transversely betwen its ends as indicated at 20, 21, 22, and also bent transversely at 23 to form a chin rest 24. A longitudinal fold 25 is formed approximately midway between the longitudinal edges of the two legs, said longitudinal fold extending from near the transverse bends 20, 22, upwardly toward the chin rest bend 23 or to the free edge of the other leg. In this embodiment, the convex surfaces of the folds 25 in the two legs may face away from each other or may face each other, as desired for the particular case. The splint described as applied to the chest and neck of the patient cooperates with a similar splint located on the back and neck, the two being held in operative positions by cords 26.

Apertures at opposite ends of the strip 10 are designated 17.

I claim:

1. A splint for use on a body extremity comprising
   a. An elongated rectangular flat strip of malleable and foldable metal having a width sufficient to substantially embrace the major width of the extremity and of a thickness insufficient to provide requisite rigidity for a splint,
   b. a transverse bend formed in the strip which shapes the strip into two legs connected by a curved portion, and
   c. a longitudinally extending rigidity-providing bend located generally midway between the longitudinal edges of the legs and extending from the ends of the legs to near the opposite sides of the transverse bend, the leg material at opposite sides of the longitudinal bend being U-shaped and extending at an obtuse angle, said longitudinally bent legs having non-uniform cross sections which permit circulation of air between the splint surfaces and skin of the splinted extremity, and said longitudinally bent legs having splint-serving rigidity at and adjacent to said longitudinal bend.

2. The splint defined by claim 1, which is provided with a coating sufficiently flexible to bend with the strip without cracking or separating therefrom, the coating being non-allergenic and radiolucent polyvinyl chloride.

3. A support for use adjacent the head of a patient, comprising
   a. an elongated rectangular flat strip of malleable metal having a thickness which is relatively small compared to its width, whereby its stiffness in the direction perpendicular to its sides is minor and may be readily deformed manually,
   b. a transverse bend formed between its ends into a bight portion and legs lying generally parallel,
   c. said support adapted to lie against the chest of the patient, the upper end thereof being shaped to conform with and support the chin,
   d. another like support adapted to lie against the back of the patient having an upper end shaped to conform to the neck and occiput,
   e. means adapted to extend over the shoulders of the patient and secured to both supports for preventing downward movement thereof, whereby the neck of the patient is restrained against undesired movement, and
   f. bends in the legs to provide curved cross sections for increasing the stiffness thereof.

4. The method of applying a splint to an injured extremity which comprises the steps of
   a. providing an elongated flat rectangular strip of malleable metal,
   b. manually folding the strip between its ends and forming a transverse curved area and two generally parallel legs connected by said curved area,
   c. manually folding or bending the legs longitudinally approximately midway between their longitudinal edges, said fold or bend extending longitudinally from the leg ends to near the opposite sides of said transversely curved area, said longitudinal bend or fold merging into said area, thereby forming non-uniform cross sections in said legs, and causing the leg material adjacent opposite sides of said longitudinal bend to extend at obtuse angles and impart splint-serving rigidity to said legs,
   d. applying the legs to an injured extremity by bringing the facing surfaces of the legs into interrupted contact with the skin of the extremity, and
   e. applying a bandage or tape to retain the splint on the extremity.

5. The method defined by claim 4, which includes the step of manually molding the splint legs slightly to the extremity after application of the longitudinally bent legs to the extremity.

* * * * *